United States Patent [19]

DeLuca et al.

[11] 4,279,826

[45] Jul. 21, 1981

[54] 23,25-DIHYDROXYVITAMIN $D_3$

[75] Inventors: Hector F. DeLuca; Heinrich K. Schnoes; Yoko Tanaka; Joseph K. Wichmann, all of Madison, Wis.

[73] Assignee: Wisconsin Alumni Research Foundation, Madison, Wis.

[21] Appl. No.: 189,481

[22] Filed: Sep. 22, 1980

[51] Int. Cl.$^3$ ............................................. C07J 9/00
[52] U.S. Cl. ................................. 260/397.2; 260/975; 260/397.3
[58] Field of Search ...................................... 260/397.2

[56] References Cited

U.S. PATENT DOCUMENTS

| | | | |
|---|---|---|---|
| 4,021,423 | 5/1977 | Baggiolini et al. | 260/397.2 |
| 4,028,349 | 6/1977 | Partridge, Jr. et al. | 260/239.5 SD |

*Primary Examiner*—Elbert L. Roberts
*Attorney, Agent, or Firm*—Howard W. Bremer

[57] ABSTRACT

23,25-Dihydroxyvitamin $D_3$ a new derivative of vitamin $D_3$. The compound is the 23-hydroxylated analog of biologically potent 23-hydroxycholecalciferol and by virtue of such structural similarity should find application as a substitute for such compound or for vitamin $D_3$.

1 Claim, No Drawings

23,25-DIHYDROXYVITAMIN D₃

The invention described herein was made in the course of work under a grant or award from the Department of Health and Human Services.

This invention relates to a novel derivative of vitamin $D_3$.

More specifically this invention relates to a novel dihydroxylated derivative of vitamin $D_3$.

Vitamin $D_3$ is a well-known agent for the maintenance of calcium and phosphorus homeostasis in animals or humans, and is widely used therapeutically for the prevention of rickets and other bone diseases. It has now been clearly established that the biological effectiveness of vitamin D in the animal or human depends upon its being metabolically converted to 25-hydroxyvitamin $D_3$ which intermediate compound undergoes further side chain hydroxylation in vivo to 24,25-dihydroxyvitamin $D_3$ and 25,26-dihydroxyvitamin $D_3$. The foregoing metabolically produced derivatives have been isolated and characterized and shown to exhibit pronounced biological activity.

A new side chain-hydroxylated vitamin D compound has now been found. This novel compound is characterized by hydroxy substitution at carbons 23 and 25 and can be represented by the formula shown below and can alternatively be referred to as 23,25-dihydroxycholecalciferol, 23,25-dihydroxyvitamin $D_3$ or 23,25-DHCC.

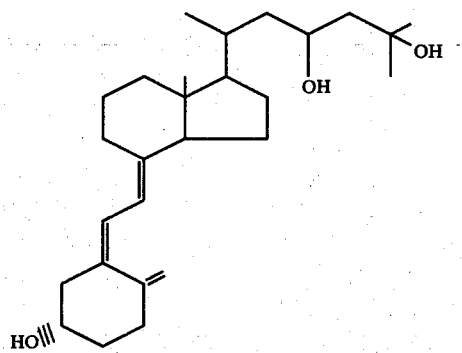

23,25-dihydroxyvitamin $D_3$, was prepared from 25-hydroxyvitamin $D_3$ by in vitro enzymatic hydroxylation, using a kidney homogenate system prepared from the kidneys of chickens fed a vitamin D-supplemented diet. The required kidney homogenate was prepared as follows:

Single-comb White Leghorn chicks (Northern Hatcheries, Beaver Dam, Wis.) were fed a normal diet for 10 weeks and given $10^5$ I.U. vitamin $D_3$ per day for 3 days followed by $1.5 \times 10^7$ I.U. for 1 day, 4 days prior to sacrifice. The chickens were killed, their kidneys removed and a 20% (w/v) homogeneous was prepared in ice-cold buffer solution containing 0.1 M phosphate buffer (pH 7.4) and 0.25 M sucrose.

This kidney homogenate was then used for the preparation of 23,25-dihydroxyvitamin $D_3$ according to the following procedure:

Three ml of the homogenate (containing 600 mg of tissue) was placed in a 125 ml Erlenmeyer flask. To this homogenate was then added 1.5 ml of 0.1 M phosphate buffer (pH 7.4) containing 22.4 mM glucose-6-phosphate, 20 mM ATP (adenosine triphosphate), 160 mM nicotinamide, and 0.4 mM NADP (nicotinamide adenine dinucleotide phosphate), and 1.5 ml of a salt solution containing 0.1 M KCl, 5 mM $MgCl_2$, 25 mM succinate, 10 μg DPPD (N,N'-diphenyl-p-phenylene diamine) and 5 units of glucose-6-phosphate dehydrogenase. The reaction was initiated by addition of 80 μg 25-hydroxyvitamin $D_3$ dissolved in 20 μl 95% ethanol. The mixtures were incubated at 37° C. with shaking at 100 oscillation/min for 2 hours under an atmosphere of air. The reaction was stopped by addition of a methanol:chloroform mixture. The incubation mixture was transferred to a phase separating funnel and the organic phase was collected. The aqueous phase was extracted once more with methanol/chloroform mixture, and the organic extracts were pooled and solvent evaporated.

The residue was dissolved in $CHCl_3$/hexane (65/35) and applied to a Sephadex LH-20 column (0.7×14 cm) packed and eluted in the same solvent. The first 11 ml of eluant was discarded and the next 20 ml of eluant was pooled.

After evaporation of solvent the residue was further purified on high pressure liquid chromatography (HPLC) as follows: The sample was applied onto a silica gel column (4.6 mm×25 cm, Zorbax-Sil, a product marketed by Dupont Instruments, Wilmington, Del.) operated under pressure of 100 psi and a flow rate of 2 ml/min in a model ALC/GPC 204 chromatograph (Waters Associates, Medford, Mass.) equipped with a UV monitor operating at 254 nm. The column was eluted with 6% 2-propanol in hexane. The desired product was eluted at 24–27 ml. The collected product was then chromatographed on a reverse phase HPLC system using a Lichrosorb RP-18 column (0.46×25 cm, a product of E. Merck, Darmstadt, West Germany) and 25% $H_2O$ in MeOH was eluting solvent. The desired product eluting at 40–44 was collected and further purified by HPLC using the silica gel column (Zorbax-Sil) and conditions as described above. The resulting purified product was then subjected to physical characterization.

Characterization of the product as 23,25-dihydroxyvitamin $D_3$

UV spectrophotometry of the compound in methanol showed a typical vitamin $D_3$ absorption maximum at 265 nm and a minimum at 228 nm indicating the presence of an intact 5,6-cis-triene chromophore in the product. The mass spectrum of the compound exhibited a molecular ion at m/e 416 as expected for a derivative of 25-hydroxyvitamin $D_3$ bearing an additional hydroxy function. The presence of this additional hydroxy function in the side chain was evident from the peaks at m/e 271 and 253 (271-$H_2O$), and the characteristic ions at m/e 136 and 118 confirmed an unaltered ring A and triene structure. The position of the side chain hydroxy groups was established by the mass spectrum of the tris-trimethylsilyl ether derivative of the compound. The spectrum showed a moleculor ion at m/e 632 as required for a tri-silylated derivative of 23,25-dihydroxy-vitamin $D_3$. The spectrum also showed characteristic side chain cleavage peaks at m/e 131 $((CH_3)_2C=O^+Si(CH_3)_3)$ which established the presence of a hydroxy group at C-25, and at m/e 487 (M+ −145) which proves the presence of a second hydroxyl at carbon 23.

These data therefore established the structure of this new vitamin $D_3$ derivative as 23,25-dihydroxyvitamin $D_3$.

Since the identified compound is the 23-hydroxylated analog of the biologically potent 25-hydroxy vitamin $D_3$, by virtue of such structural similarity the compound of this invention should find application as a substitute for 25-hydroxy vitamin $D_3$ in various therapeutic applications or as a substitute for vitamin $D_3$.

What is claimed is:

1. 23,25-dihydroxyvitamin $D_3$.

* * * * *